United States Patent [19]

Andress, Jr.

[11] 4,148,605

[45] Apr. 10, 1979

[54] RUST INHIBITOR AND COMPOSITIONS THEREOF

[75] Inventor: Harry J. Andress, Jr., Wenonah, N.J.

[73] Assignee: Mobil Oil Corporation, New York, N.Y.

[21] Appl. No.: 730,551

[22] Filed: Oct. 7, 1976

[51] Int. Cl.² ............................ C10L 1/18; C10L 1/22
[52] U.S. Cl. ................................. 422/7; 44/63; 44/77; 252/51.5 A; 252/56 D; 260/308 B; 560/190; 260/404.8
[58] Field of Search ....................... 260/485 R, 308 B; 21/2 TR; 560/190

[56] References Cited

U.S. PATENT DOCUMENTS

| | | | |
|---|---|---|---|
| 3,117,091 | 1/1964 | Staker | 260/485 R |
| 3,155,685 | 11/1964 | Prill et al. | 260/485 R |
| 3,487,101 | 12/1969 | Volker et al. | 260/485 R |

*Primary Examiner*—Paul M. Coughlan, Jr.
*Attorney, Agent, or Firm*—Charles A. Huggett; Raymond W. Barclay; Howard M. Flournoy

[57] ABSTRACT

Novel dicarboxylic ester-acids resulting from the condensation of an alkenylsuccinic anhydride with an aliphatic hydroxy acid having from 2 to about 18 carbon atoms and amine salts of said ester-acid are useful as rust or corrosion inhibitors in organic compositions.

13 Claims, No Drawings

RUST INHIBITOR AND COMPOSITIONS THEREOF

BACKGROUND OF THE INVENTION

Field of the Invention

This invention relates to anti-rust/anti-corrosion inhibitors, to organic compositions comprising liquid and solid organic media which contain a minor amount of said inhibitors and to a method of inhibiting the formation of rust and/or corrosion of metallic surfaces in contact with such organic compositions.

DESCRIPTION OF THE PRIOR ART

It is well known that certain types of materials are normally susceptible to deterioration by oxidation or by corrosion when coming into contact with various organic media. Organic compositions in both the liquid and solid form can induce such corrosion or oxidation. For example, it is known that liquid hydrocarbons in the form of various fuel oils, such as petroleum distillate hydrocarbon fuels; lubricating oils or greases tend to accumulate considerable quantities of water when maintained for long periods of time in storage vessels; and when subsequently brought into contact with metal surfaces in their functional environments, deterioration of said surfaces as a result of rust and corrosion occurs. In addition, where such lubricating oils are incorporated into lubricants in the form of greases, similar deleterious results are encountered.

To overcome this very serious problem many materials have been proposed for use as rust inhibiting additives in organic compositions. For example, U.S. Pat. No. 2,668,100 proposed the use of certain carboxylic monocarboxy acid salts of glyoxalidines; U.S. Pat. No. 3,365,477 proposed the use of metal salts of succiniamic acids and U.S. Pat. No. 3,485,858 the use of metal alkyl or alkoxy metal alkyl, ester tetrapropenyl succinates.

SUMMARY OF THE INVENTION

This invention relates to the discovery that certain novel alkenylsuccinic ester-acids and amine (e.g., tolyl triazole) salts thereof, are effective rust or corrosion inhibitors, that organic compositions containing them substantially prevent and/or reduce the formation of rust on metallic surfaces with which the compositions are in contact; and to a method of their use in preventing and/or inhibiting the formation of rust on metal surfaces in contact with organic media such as petroleum distillate hydrocarbon fuel oils, gasoline, naphthas, various burning oils, diesel fuel oil, furnace oils, oils of lubricating viscosity and greases derived from both synthetic and mineral oil basestocks.

The anti-rust additives in accordance with this invention are novel compounds having the following general formula:

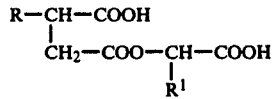

where R is alkenyl having from about 4 to about 24 carbon atoms and $R^1$ is selected from the group consisting of H, $C_1$-$C_{16}$ alkyl, aryl, alkaryl, carboxy, $C_1$-$C_{16}$ alkyl carboxy and combinations thereof having up to about 16 carbon atoms. R preferably contains from about 8 to about 16 carbon atoms and $R^1$ is preferably alkyl and contains from 1 to about 4 carbon atoms.

This application is further concerned with compositions comprising a major proportion of a liquid or solid organic material normally disposed to causing or inducing deterioration by rust or corrosion when in contact with metallic surfaces and a minor amount sufficient to inhibit said deterioration, of the above-noted compounds.

Additionally, this application is also concerned with a method of preventing or inhibiting rust or corrosion of metal when in contact with moisture and other similar deleterious media comprising contacting metallic surfaces with an organic material containing a minor amount, sufficient to inhibit rust or corrosion, of the above described novel dicarboxylic ester-acids or amine salts thereof.

Generally, the compounds in accordance with this invention are prepared by condensing an appropriate alkenyl-succinic anhydride with a suitable aliphatic hydroxy acid, e.g., lactic acid, under ambient pressure (although the reaction may be carried out under pressure if so desired) at a temperature of from about 105° to about 130° C. Usually no solvent is used but if it is so desired any suitable hydrocarbon diluent, e.g., xylene may be advantageously used. The amine salts thereof are then prepared by reacting the ester-acid under similar temperature and pressure conditions with an amine, e.g., tolyl triazole, in a mole ratio of amine to ester-acid of from about 1:1 to about 2:1.

The aliphatic hydroxy acids in accordance with this invention have from 2 to about 18 carbon atoms and include monocarboxylic and dicarboxylic hydroxy acids as well as monohydric, dihydric or polyhydric hydroxy acids such as glycolic, lactic, hydroxybutyric, mandelic, glyceric, malic, hydroxystearic, tartaric and the like. Lactic acid is preferred.

Suitable amines include $NH_3$, $C_1$-$C_{24}$ aliphatic amines straight or branched, primary, secondary or tertiary such as ethylenediamine, diethylamine, methylamine, dimethyl-sec-butylamine, triazoles, aryl amines such as aniline and N-methylaniline, diphenylamine, naphthylamines, fatty amines, substituted amines such as chloroaniline, and the like. Preferred are triazoles having the following general formula:

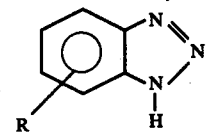

where R is H or alkyl of 1-16 carbon atoms; especially preferred are benzotriazole and tolyl triazole.

As previsouly stated, the alkenyl substitutent of the succinic anhydride compounds in accordance with the invention have from 4 to about 24 carbon atoms. Accordingly suitable succinic anhydrides for use herein include butenyl, isobutenyl, heptenyl, nonenyl, dodecenyl succinic anhydride, etc. Preferred is dodecenyl succinic anhydride.

The amount of additive added to a particular composition will vary dependent on the intended use of such composition and the specific nature of the organic media. Usually, however, the rust and corrosion inhibiting compositions disclosed and claimed herein will contain from about 0.1 to about 100.0 lbs. of the additive per 1000 bbls of the total composition.

DESCRIPTION OF SPECIFIC EMBODIMENTS

The following examples will serve to illustrate the preparation of the novel compounds of the present invention, exemplified are dicarboxylic ester-acids and their corresponding amine (e.g. benzotriazole) salts. As mentioned hereinabove, the ester-acid compounds according to the invention are preferentially formed by the condensation of an alkenylsuccinic anhydride with lactic acid. In Example 1 below, substantially equimolar amounts of the reactants are used.

EXAMPLE 1

A mixture of 266 grams (1 mol) of dodecenyl succinic anhydride and 90 grams (1 mol) lactic acid was gradually heated to 120°–125° C. with stirring and held there for about four hours to form the ester-acid.

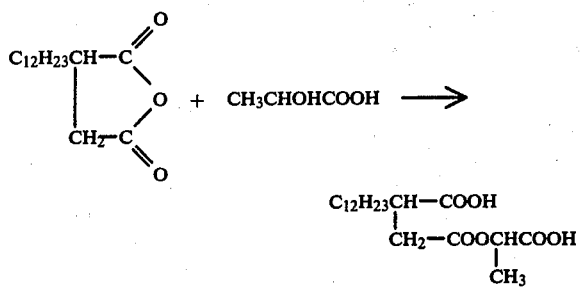

EXAMPLE 2

A mixture of 178 grams (0.5 mol) of the product from Example 1 and 67 grams (0.5 mol) of tolyl triazole was stirred and gradually heated to 110° C. and held there for about two hours and then further heated to 125° C. and held there for about two hours to form as the final product—a mono amine salt.

EXAMPLE 3

A mixture of 178 grams (0.5 mol) of the product from Example 1 and 133 grams (1.0 mol) of tolyl triazole was stirred with gradual heating to 115° C. for about three hours to form the final product—a diamine salt.

The compounds of Examples 1–3 were then tested in a gasoline blend in accordance with ASTM Rust Test D-665 with results as given in the Table below. (The gasoline blend had the below described general properties).

The method used for testing anti-rust properties of the gasoline blend was the aforementioned ASTM Rust Test D-665 operated for 48 hours at 80° F. using distilled water. This is a dynamic test that indicates the ability to prevent rusting of ferrous metal surfaces in pipelines, tubes, etc. Blends of the additives described below in the fuel were subjected to the ASTM Rust Test D-665. The results obtained are set forth in the following Table.

Inhibitors according to the invention were blended in a gasoline comprising 40% catalytically cracked component, 40% catalytically reformed component, and 20% alkylate—approximately 90°–410° F. boiling range.

TABLE

| Compound | A.S.T.M. Rust Test D-665 Conc. lbs./1000 bbls. | Rust Rating |
|---|---|---|
| Base Fuel | 0 | Heavy Rust |
| Base Fuel Plus Example 1 | 1 | No Rust |
| Base Fuel Plus Example 2 | 1 | No Rust |
| Base Fuel Plus Example 3 | 1 | No Rust |

As indicated, an identical blend without any of the novel additive inhibitors of the invention was also tested under the same conditions. The results as shown in the Table clearly demonstrate that the compounds in accordance with the invention completely prevented the formation of rust while the gasoline blend without the additive resulted in the formation of heavy rust.

It is understood that the improved compositions in accordance with the present invention, if so desired, contain various other additives or mixtures thereof to further enhance said compositions' properties. Such additives include, for example, antioxidants, detergents, dispersants, stability improvers and the like.

Although described with preferred embodiments, it is also understood that various modifications may be resorted to without departing from the spirit and scope of the invention as will be readily apparent to one of ordinary skill in the art.

What is claimed is:

1. A compound having the following general structure:

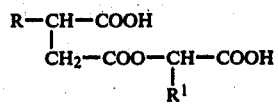

where R is alkenyl having from about 4 to about 24 carbon atoms and R' is $C_1$-$C_{16}$ alkyl.

2. The compound of claim 1 where R is from about 8 to about 16 carbon atoms and $R^1$ is alkyl from 1 to about 4 carbon atoms.

3. The compound of claim 2 where R has 12 carbon atoms and $R^1$ has 1 carbon atom.

4. A composition comprising a major proportion of a liquid or solid organic material, which normally induces deterioration of metallic surfaces when in contact therewith and a minor amount, sufficient to inhibit said deterioration, of a compound having the following general structure:

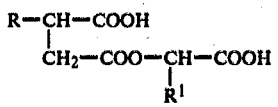

where R is alkenyl of from about 4 to about 24 carbon atoms and $R^1$ is $C_1$-$C_{16}$ alkyl.

5. An amine salt produced by reacting the compound of claim 1 with a triazole having the formula:

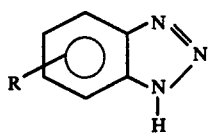

wherein R is H or alkyl of 1-16 carbon atoms under ambient pressure and at a temperature of from about 105° to about 130° C.

6. The amine salt produced by reacting said compound as in claim 5 with tolyl triazole in a mole ratio of said triazole to said compound of from about 1:1 to about 2:1.

7. The amine salt of claim 6 which is a mono-amine resulting from the reaction of tolyl triazole and the compound of claim 1 in a 1:1 mole ratio of said triazole to said compound.

8. The amine salt of claim 6 which is a diamine resulting from the reaction of triazole and the compound of claim 1 in a 2:1 mole ratio of said triazole to said compound.

9. The composition of claim 4 where R is from about 8 to about 16 carbon atoms and $R^1$ is alkyl of from 1 to about 4 carbon atoms.

10. The composition of claim 9 where R has 12 carbon atoms and $R^1$ has 1 carbon atom.

11. The composition of claim 4 where the organic material is a gasoline.

12. A method of inhibiting rust or corrosion of metallic surfaces susceptible to contamination by contact with moisture or moisture containing organic media comprising contacting said metallic surfaces with an organic material containing a minor amount sufficient to inhibit rust or corrosion of said metallic surfaces, with a compound as defined in claim 1.

13. The method of claim 12 where the organic material containing said minor amount of said compound is a gasoline.

* * * * *